(12) United States Patent
Byun et al.

(10) Patent No.: US 7,129,224 B1
(45) Date of Patent: *Oct. 31, 2006

(54) HYDROPHOBIC MULTICOMPONENT HEPARIN CONJUGATES, A PREPARING METHOD AND A USE THEREOF

(75) Inventors: Young Ro Byun, Kwangju (KR); Hyun Tae Moon, Kwangju (KR)

(73) Assignee: Mediplex Corporation, Korea (KR)

( * ) Notice: Subject to any disclaimer, the term of this patent is extended or adjusted under 35 U.S.C. 154(b) by 0 days.

This patent is subject to a terminal disclaimer.

(21) Appl. No.: 10/333,641

(22) PCT Filed: Nov. 3, 2000

(86) PCT No.: PCT/KR00/01255

§ 371 (c)(1),
(2), (4) Date: Jan. 21, 2003

(87) PCT Pub. No.: WO02/34312

PCT Pub. Date: May 2, 2002

(30) Foreign Application Priority Data

Oct. 24, 2000  (KR) .................. 10-2000-0062668

(51) Int. Cl.
*A61K 31/727* (2006.01)
*C09D 105/10* (2006.01)
*C08L 5/10* (2006.01)
*C09J 105/10* (2006.01)

(52) U.S. Cl. .................. 514/56; 106/162.2; 536/21
(58) Field of Classification Search ................ 530/300, 530/333, 322; 514/2, 23
See application file for complete search history.

(56) References Cited

U.S. PATENT DOCUMENTS

| | | | | |
|---|---|---|---|---|
| 5,955,588 A | * | 9/1999 | Tsang et al. .................. 536/21 |
| 6,071,532 A | * | 6/2000 | Chaikof et al. ............. 424/450 |
| 6,229,009 B1 | * | 5/2001 | Lambert et al. .......... 536/123.1 |
| 6,245,753 B1 | | 6/2001 | Byun et al. .................... 514/56 |
| 6,589,943 B1 | | 7/2003 | Byun et al. .................... 514/56 |
| 6,702,850 B1 | * | 3/2004 | Byun et al. ................. 623/1.44 |

FOREIGN PATENT DOCUMENTS

| | | | | |
|---|---|---|---|---|
| JP | 53-57288 | | 5/1978 | |
| JP | 1-262869 | | 10/1989 | |
| KR | 99-87944 A | | 12/1999 | |
| WO | WO 9808897 | * | 3/1998 | .............. 536/123.1 |

OTHER PUBLICATIONS

"Multifunctional" Encarta® World English Dictionary, North American Edition. Accessed Apr. 25, 2005. Microsoft Corp.*
CJ van Delden, et al. J. Biomater. Sci. Polymer Edn. (1996) 7(8), pp. 727-740.*
Grainger, D.W. et al. Poly(dimethylsiloxane)-poly(ethylene oxide)-heparin block copolymers. I Synthesis and characterization. *Journal of Biomedical Materials Research*, 22, 231-249 (1988).
Kim, Young Jin et al. Surface characterization and in vitro blood compatibility of poly(ethylene terephthalate) immobilized with insulin and/or heparin using plasma glow discharge. *Biomaterials*, 21, 121-130 (2000).
Marconi, W. et al. New polyurethane compositions able to bond high amounts of both albumin and heparin. *Biomaterials*, 17, 1795-1802 (1996).

* cited by examiner

*Primary Examiner*—Cecilia J. Tsang
*Assistant Examiner*—Andrew D. Kosar
(74) *Attorney, Agent, or Firm*—Clayton, Howarth & Cannon, P.C.

(57) ABSTRACT

The present invention provides hydrophobic heparin conjugates that are soluble in organic solvents but not in water, a method of preparing them, and a method of using them. Particularly, the present invention provides hydrophobic heparin conjugates that are prepared by covalently binding a polymer to heparin and a hydrophobic agent to the polymer. The hydrophobic heparin conjugates of the present invention maintain a good antithrombogenic effect and are insoluble in water due to their hydrophobicity, so they can be effectively used as coating agents for modifying the surfaces of medical devices.

12 Claims, No Drawings

HYDROPHOBIC MULTICOMPONENT HEPARIN CONJUGATES, A PREPARING METHOD AND A USE THEREOF

CROSS-REFERENCE TO RELATED APPLICATIONS

This application is the National Stage of International Application No. PCT/KR00/01255, filed Nov. 3, 2000, which was published in English under PCT Article 21(2), which is hereby incorporated in its entirety, which claimed priority to Korean Patent Application No. KR 2000/62668, filed Oct. 24, 2000.

STATEMENT REGARDING FEDERALLY SPONSORED RESEARCH OR DEVELOPMENT

Not applicable.

BACKGROUND OF THE INVENTION

The present invention relates to hydrophobic multicomponent heparin conjugates, which are soluble in certain organic solvents but not in water, and to methods of using and making thereof. Particularly, the present invention relates to hydrophobic multicomponent heparin conjugates that are prepared by covalently binding polymeric and hydrophobic materials to heparin and that are used for treatment of patients as a antithrombogenic agent.

Thromboresistence of vascular walls requires an endothelial lining that is compatible with platelets and the plasma coagulation system. Unlike artificial vascular materials, endothelial linings do not induce serine protease activity during the coagulation process. However, when coagulability of blood is increased, the endothelium inactivates thrombin and other possible coagulation factors. Generally, the inflow site of thrombin is known to be at the surface of endothelium cells (B. Awbrey et al. *J. Biol. Chem.*, 254, 4092–4095, 1979), and the glycosaminoglycan layer on endothelial cells is also known to have thrombin-binding sites. It is reported that if those thrombin binding sites are bound to enzymes such as serine protease, the enzymes are inactivated by antithrombin III in blood serum (C. Busch et al., *J. Clin. Invest.*, 726–729, 1982; M. Dryjski et al., *Thromb. Res.*, 32, 355–363, 1983).

After it was reported that an analogous structure for antithrombin binding exists in heparin molecules (J. A. Marcum et al., *J. Clin. Invest.*, 74, 341–350, 1984; J. A Marcum et al., *Biochem. Biophys. Res. Comm.*, 126, 365–372, 1985), methods for introducing heparin into or on the surface of solid materials to produce endothelium-like thromboresistent properties was soon developed and commercialized. Artificial surfaces, which have obtained endothelium-like thromboresistent properties by using heparin and the like can be widely used for the development of medical techniques.

Among those studies, various methods for improving blood compatibility of macromolecular surface using heparin were developed. Grode et al. synthesized heparin-silicon rubber using cyanuric chloride and radiation grafting (Grode et al., *J. Biomed. Mater. Res. Symp.*, 3, 77–84, 1972). Merrill et al. also synthesized a conjugate wherein polyvinyl alcohol was covalently bound to heparin by glutaraldehyde cross linking (Merrill et al., *J. Appl. Physiol.*, 29, 723–728, 1970). Eriksson and Gillerg developed a cross-linked heparin monomer in which anionic heparin was absorbed on the surface of polypropylene by heparin cross linking and use of a cationic surfactant (Eriksson and Gillerg, *J. Biomed. Mater. Res.*, 1, 301–312, 1967).

Goosen and Sefton synthesized heparinized a styrene-butadiene-styrene elastomer (Goosen and Sefton, *Thromb. Res.*, 20, 543–554, 1980). And, Miyura et al. designed a method of prolongation of plasma recalcification by fixing heparin on Sepharose® or polyhydroxymethacrylate (Miyura et al., *J. Biomed. Mater. Res.*, 14, 619–630, 1980).

Jacobs et al. synthesized a covalently bonded complex of heparin and prostaglandin E1 (Jacobs et al., *J. Biomed. Mater. Res.*, 23, 611–630, 1989). The above heparin complex was fixed on urethane by diamino-terminated polyethylene oxides, and this fixed complex was very effective for prohibiting thrombin formation. Hennink et al. developed a covalently bonded complex of heparin and human serum albumin (Hennink et al., *Thromb. Res.*, 29, 1–13, 1983). This complex increased blood compatibility of macromolecular surfaces that were in contact with blood.

Nagaoka et al. reported the results of animal experiments that showed that a polyethylene oxide (PEO) hydrophilic spacer fixed on a macromolecular surface inhibited the attachment of platelets by absorption of blood proteins and dynamic repulsion (Nagaoka et al., *Trans. Am. Soc. Artif. Intern. Organs.*, 10, 76—76, 1987). The inhibitory effect on platelet attachment by a spacer fixed on a heparinized surface was confirmed by Kim and Ebert (Kim and Ebert, *Thromb. Res.*, 26, 43–57, 1982). They proved that nticoagulant activity of fixed heparin increased according to the length of spacer.

Further, Tay et al. showed that 1) a long spacer, such as PEO, made binding heparin with antithrombin III and thrombin easier; 2) heparin coupled to end groups of polyvinylalcohol was more accessible than heparin coupled to amino groups on non-terminal units of heparin macromolecules; and 3) heparin units on the surface obstructed the access of antithrombin III and thrombin (Tay et al., *Biomaterials*, 10, 11–15, 1989).

Schmer covalently bound heparin to agarose by using spacers such as thiophosgene or carbodiimide (Schmer, *Trans. Am. Soc. Artif. Intern. Organs.*, 18, 321–324, 1972), and this spacer-fixed heparin had advanced binding capacity to antithrombin III.

Danishefsky and Tzeng produced heparin-agarose macromolecules by using an aminoethyl spacer (Danishefsky and Tzeng, *Thromb. Res.*, 4, 237–246, 1974). Park et al. fixed heparin on a biomer by using a PEO spacer, and they reported that the length of such spacers should be at least 3,400 Daltons to optimize anticoagulation activity of the fixed heparin (Park et al., *J. Biomed. Mater. Res.*, 22, 977–992, 1988). Also, heparin was fixed on the surface of spacers to optimize anticoagulation activity and to amplify surface density of the spacers. (Lin et al., *J. Biomed. Mater. Res.*, 25, 791–795, 1991; Piao et al., *Trans. Am. Soc. Artif. Intern. Organs.*, 38, 638–643, 1992).

Moreover, spacer systems using heparin were used for synthesis of copolymers. Triblock copolymers such as PEO-PDMS-heparin and PDMS-PEO heparin were synthesized (Grainger et al., *J. Biomed. Mater. Res.*, 22, 231–249, 1988). These triblock copolymers coated on a segmented polyurethane surface increased nonthrombogenicity even under low flow. Vulic et al. reported a method of synthesizing polyurethane-PEO-heparin (Vulic et al., *J. Polym. Sci. A, Polym. Chem.*, 26, 381–391, 1988), which was a modification of the solvent casting method. According to this method, coating was easy but synthesis of the heparin complex with polyurethane or polyethylene glycol was not due to problems of low efficiency and of requiring an excessive amount of solvent to suppress cross linking of heparin during the synthesis process.

To overcome the foregoing and other disadvantages, a method of making a heparin complex, comprising heparin and hydrophobic macromolecules, has been developed in which heparin is combined first with a macromolecule having multi-functional groups and then with hydrophobic materials. The result is a synthesized hydrophobic multi-component heparin conjugate that is soluble in organic solvents but not in water. Finally, the hydrophobic multi-component heparin conjugates of the present invention can easily be coated on the surface of all medical instruments comprising macromolecules or metals, and such coated instruments exhibit high anti-thrombosis.

BRIEF SUMMARY OF THE INVENTION

The objective of this invention is to provide hydrophobic multicomponent heparin conjugates that are soluble in specific organic solvents but not in water, and methods of preparing and using thereof.

DETAILED DESCRIPTION

To accomplish those objectives, the present invention provides hydrophobic muiticomponent heparin conjugates in which heparin is coupled with macromolecules and hydrophobic materials.

The present invention also provides a method of the preparing the hydrophobic multicomponent heparin conjugates.

This invention also provides a method of use of the hydrophobic multicomponent heparin conjugates as a coating agent for the surface modification of all medical instruments or artificial organs.

Hydrophobic multicomponent heparin conjugates of the present invention are heparin coupled with macromolecules containing multi-functional groups, in which the binding ratio of heparin and macromolecule can be controlled, and wherein amine groups among the functional groups of heparin are used for binding with macromolecules.

Heparin has carboxyl groups, hydroxyl groups, sulfonic acid groups, and amine groups as functional groups. All the functional groups except amine groups exist in the active site of anti-thrombosis; thus, when those functional groups are used for binding with macromolecules, these heparin-macromolecule conjugates lose their anti-thrombosis activity.

Synthetic macromolecules, proteins, biopolymers, and their mixtures can be used as macromolecules containing the aforementioned multi-functional groups. For synthetic macromolecules, polydienes, polyalkenes, polyacetylenes, polyacrylic acid and its derivatives, poly α-substituted acrylic acid and its derivatives, polyvinyl ethers, polyvinylalcohol, polyvinyl halides, polystyrene and its derivatives, polyoxides, polyethers, polyesters, polycarbonates, polyamides, polyamino acids, polyureas, polyurethanes, polyimines, polysulfides, polyphosphates, polysiloxanes, polysilsesquioxanes, polyheterocyclics, cellulose and its derivatives, polysaccharides, and their copolymers or derivatives can be used. For proteins, protamine, polylysine, polyaspartic acid, polyglutamic acid and its derivatives or copolymers can be used. For biopolymers, polysaccharides, gelatin, collagen, alginate, hyaluronic acid, alginic acid, carrageenan, chondroitin, pectin, chitosan, and their derivatives or copolymers can be used. Apart from these mentioned, all macromolecules containing multi-functional groups can be used.

Hydrophobic multicomponent heparin conjugates of the present invention are produced by coupling heparin and macromolecules containing multi-functional groups, and then the hydrophobic material is bound thereto. As a result, a heparin molecule forms a conjugate by binding with many macromolecules containing multi-functional groups, to which hydrophobic materials are attached. Thus, many functional groups, which do not participated in binding, can be reacted with a hydrophobic material. Finally, hydrophobic multicomponent heparin conjugates of the present invention are hydrophobic because heparin is coupled to a hydrophobic macromolecule.

Hydrophobic multicomponent heparin conjugates of the present invention are not soluble in water but in specific organic solvents such as tetrahydrofuran and DMAC (dimethylacetamide). Thus, hydrophobic multicomponent heparin conjugates of the present invention can easily be synthesized by the solvent evaporation method and also can easily be coated on the surface of macromolecules or metals by the dip coating or spray method. For clinical usage, the hydrophobic multicomponent heparin conjugates of the present invention are stable because of their water insolubility.

Heparin in the hydrophobic multicomponent heparin conjugates of the present invention sustains its anti-thrombosis activity even after it is coated on substrates, so it can inhibit blood clotting that might arise on the surface of coated substrates. Therefore, the hydrophobic multicomponent heparin conjugates of the present invention improve the anti-thrombosis effect of the coated surface. On the other hand, heparin is highly anionic, and thus significantly decreases the frictional coefficient of coated surfaces while increasing the water-absorption capacity of such surfaces. Thus, the quality of artificial organs and medical instruments, such as catheters or insertion tubes, which are in contact with blood, can be improved by modification of their surfaces by coating with the hydrophobic muiticomponent heparin conjugates of the present invention, thereby minimizing side effects caused by thrombi.

The present invention also provides a method of preparing the hydrophobic multicomponent heparin conjugates including steps as follows:
1) Activation of macromolecules;
2) Binding of heparin and activated macromolecule; and
3) Binding of hydrophobic materials to the functional groups of the macromolecules bonded to heparin.

Whereas the existing method is to synthesize a triblock copolymer in which heparin is combined with polyurethane and polyethylene glycol, the method of the present invention consists of a multistep process including synthesis of a graft copolymer in which heparin is coupled to the macromolecule and hydrophobic material. According to the present invention, the macromolecule itself does not need to be hydrophobic. The structure of the hydrophobic multicomponent heparin conjugates is different from that of the triblock copolymer. The triblock copolymer has a form in which heparin is coupled to the end of a PEG-polyurethane chain, but the hydrophobic multicomponent heparin conjugates of the present invention have a form in which the macromolecule containing multi-functional groups is coupled to heparin itself and then the hydrophobic material is coupled to a functional group of the macromolecule.

Macromolecules that can be coupled to heparin according to the present invention include synthetic macromolecules, proteins, biopolymers, and mixtures thereof. Macromolecules containing multi-functional groups are preferred. Polydienes, polyalkenes, polyacetylenes, polyacrylic acid and its derivatives, poly α-substituted acrylic acid and its derivatives, polyvinyl ethers, polyvinylalcohol, polyvinyl halides, polystyrene and its derivatives, polyoxides, polyethers, polyesters, polycarbonates, polyamides, polyamino acids, polyureas, polyurethanes, polyimines, polysulfides, polyphosphates, polysiloxanes, polysilsesquioxanes, polyheterocyclics, cellulose and its derivatives, polysaccharides, and their copolymers or derivatives can be used as a synthetic macromolecule, and protamine, polylysine, polyaspartic acid, polyglutamic acid and its derivatives or copolymers can be used as a protein. Further, polysaccharides, gelatin, collagen, alginate, hyaluronic acid, alginic acid, carrageenan, chondroitin, pectin, chitosan, and their derivatives or copolymers can be used as a biopolymer. Still further, all macromolecules containing multi-functional groups can be used.

To activate these macromolecules, in the preferred embodiment of the present invention, a carboxyl group (COOH) of the macromolecule is activated by using N,N-dicyclohexylcarbodiimide (DCC), but 1-ethyl-3-dimethylaminopropyl-carbodiimide hydrochloride (EDC) or 4-p-azidosalicylamido-butylamine (ASBA) can also be used.

In step 2, it is preferred that the molecular weight of heparin is 1,000–1,000,000 Daltons, and recombinant heparin, heparin derivatives, and heparin analogues can be used with the same method. A covalent bond is formed by using a hydroxyl group, amine group, thiol group, or azide group for binding heparin with the activated macromolecules. Preferably the covalent bond is a non-degradable bond, such as an amide bond or a urethane bond, or a degradable bond, such as an ester bond or an anhydride bond.

In step 3, it is preferred that the water-solubility of the hydrophobic material that is coupled to the macromolecule is less than 100 mg/ml, and that the hydrophobic material has at least one functional group. Octadecylamine (ODA), alkanoic amine, bile acids, sterols, or alkanoic acids can be used as a hydrophobic material, and all other materials, which have the required functional groups and hydrophobicity, can be used. A covalent bond is formed by using a hydroxyl group, carboxyl group, amine group, thiol group, or azide group for binding the hydrophobic materials to the functional groups of the macromolecules coupled to heparin. Preferably the covalent bond is a non-degradable bond, such as an amide bond or a urethane bond, or a degradable bond, such as an ester bond or an anhydride bond.

The present invention also provides a method of use of the hydrophobic multicomponent heparin conjugates. As mentioned above, hydrophobic multicomponent heparin conjugates of the present invention can easily be synthesized by the solvent evaporation method, and they can easily be coated on the surface of macromolecules or metals by the dip coating or spray method. Further, for clinical usage, the hydrophobic multicomponent heparin conjugates of the present invention are stable because of their water insolubility.

Substrates coated with the hydrophobic multicomponent heparin conjugates of the present invention have high anti-thrombosis activity because they can suppress blood clotting, and they significantly decrease the frictional coefficient and increase the water-absorption capacity of coated surfaces.

Thus, artificial organs and medical instruments, such as catheters or insertion tubes, which are in contact with blood, can be improved by modification of their surfaces by coating with the hydrophobic multicomponent heparin conjugates of the present invention, and side-effects caused by thrombi can be minimized by use of the hydrophobic multicomponent heparin conjugates of the present invention.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Activation of Polyacrylic Acid

Five g of polyacrylic acid (referred to as "PAA" hereinafter) was added to 250 ml of N,N-dimethylformamide (referred to as "DMF" hereinafter) and dissolved, which thereafter was cooled in an ice bath. To the above mixed solution, 25 ml of DMF solution in which 15.5 g of N,N-dicyclohexylcarbodiimide (referred to as "DCC" hereinafter) was dissolved was immediately added. This mixture was stirred for five minutes to all the DCC to be activated, after which 25 ml of DMF solution containing 8.7 g of N-hydroxylsuccinimide (referred to as "HOSU" hereinafter) was quickly added to the above mixture. As the reaction proceeded, N,N-dicyclohexylurea (referred to as "DCUrea" hereinafter) was gradually generated and precipitated. After 24 hours of reaction, DCUrea was removed by filtering with a 0.2 μm pore size membrane, and the mixed solution was left at 5° C. for 12 hours and, thereafter, the small amount of remaining DCUrea was filtered and removed completely by the same procedure described above. Next, DMF was removed by solvent evaporation at room temperature. Next, 500 ml of methanol was added and stirred for 5 hours, after which any unreacted DCC and HOSU remaining were removed by filtering with a 0.2 μm membrane. The methanol was removed by vacuum drying at room temperature for 6 hours, and 8.7 g of white powder was finally obtained.

Example 2

Synthesis of Heparin-Polyacrylic Acid-Octadecylamine Conjugate (Heparin/PAA/ODA=1:1:20, Molar Ratio)

First, 0.11 g of activated PAA obtained according to the procedure of Example 1 was dissolved in 100 ml of DMF, into which 50 ml of distilled water containing 0.3 g of heparin was loaded for 5 minutes. Within 30 minutes after the reaction began, sediment, a product from combining heparin and activated PAA, was generated and the solution became less clear with it. Five hours later, 350 ml of THF solution containing 0.13 g of octadecylamine (referred to as "ODA" hereinafter) was gradually added into the solution for 5 minutes, and then was left to react for 5 hours at room temperature. Through the above procedure, white sediment began to be generated, and this reaction was completed within 30 minutes. After completion of the reaction, 400 ml of THF and distilled water were removed from the solution by solvent evaporation at room temperature, and the remaining unreacted ODA was removed by dialysis using cellulose ester membrane and acetone as a solvent. Thereafter, acetone was substituted with water and filtered with a 0.45 μm filter membrane, resulting in the elimination of remaining unreacted heparin. The white sediment obtained from the above reaction was vacuum dried for 12 hours. As a result, 0.45 g of white powder was obtained.

Example 3

Synthesis of Heparin-Polyacrylic Acid-Octadecylamine Conjugate (Heparin/PAA/ODA=1:5:100, Molar Ratio)

Activated PAA (0.55 g) obtained according to the procedure of Example 1 was dissolved into 100 ml of DMF, into which 50 ml of distilled water containing 0.3 g of heparin was loaded for 5 minutes. Within 30 minutes after the reaction began, sediment, a product from combining heparin and activated PAA, was generated and the solution became less clear. Five hours later, 350 ml of THF solution containing 0.67 g of ODA was slowly added into the solution for 5 minutes, and was left to react at room temperature for 5 hours. Through the above procedure, white sediment was generated, and the reaction was completed within 30 minute. On completion of the reaction, 400 ml of THF and distilled water were removed from the above solution by solvent evaporation at room temperature, and unreacted ODA was eliminated by dialysis using a cellulose ester membrane and acetone as a solvent. Thereafter, the acetone solvent was replaced with water and filtered with a 0.45 μm membrane, resulting in removing unreacted heparin. The white sediment obtained from this procedure was vacuum dried for 12 hours, from which 1.1 g of white powder was obtained.

Example 4

Synthesis of Heparin-Polyacrylic Acid-Octadecylamine Conjugate (Heparin/PAA/ODA=1:10:200, Molar Ratio)

Activated PAA (1.11 g) obtained according to the procedure of Example 1 was dissolved into 100 ml of DMF, into which 50 ml of distilled water containing 0.3 g of heparin was loaded for 5 minutes. Within 30 minutes after the reaction began, sediment, a product from combining heparin and activated PAA, was generated and the solution began to be less clear. Five hours later, 350 ml of THF solution in which 1.35 g of ODA was dissolved was gradually added into the solution for 5 minutes, after which it was left to react at room temperature for 5 hours. Finally, white sediment was generated, and the reaction was completed within 30 minutes. As the reaction was completed, 400 ml of THF and distilled water were eliminated from the mixed solution by solvent evaporation at room temperature, and unreacted ODA was also removed by dialysis using a cellulose ester membrane and acetone as a solvent. Later on, acetone solvent was substituted with water and unreacted heparin was removed by filtering with a 0.45 μm membrane. The white sediment obtained from this procedure was vacuum dried for 12 hours, from which 2.0 g of white powder was obtained.

Example 5

Activation of Deoxycholic Acid

First, 11.8 g of deoxycholic acid (referred to as "DOCA" hereinafter) was dissolved in 100 ml of DMF and cooled in an ice bath thereafter. To that mixed solution, 25 ml of DMF solution in which 7.4 g of DOC was dissolved was quickly added. On stirring for 5 minutes, DCC became activated and 25 ml of DMF solution in which 4.14 g of HOSU was dissolved was rapidly added thereto. As the reaction proceeded, DCUrea was gradually precipitated. After 24 hours of reaction, DCUrea was removed by filtering with a 0.2 μm membrane, and the solution was chilled at 5° C. for 12 hours, after which the small amount of remaining DCUrea was eliminated completely by filtering in the same manner as described above. Next, 100 ml of acetonitrile was added to the reactive solution and DMF was removed by solvent evaporation at room temperature, resulting in precipitation of a white solid. This white solid was obtained by filtering using a 0.2 μm membrane, followed by vacuum drying at room temperature for 5 hours, from which 12.5 g of activated DOCA was obtained.

Example 6

Synthesis of Hydrophobic Protamine (Protamine-DOCA)

Protamine (0.5 g) was dissolved in 50 ml of distilled water, into which 50 ml of DMF solution containing 0.27 g of activated DOCA, obtained according to the procedure of Example 5, was gradually added. The solution was maintained at room temperature for 5 hours while the coupling reaction was taking place. DMF and distilled water were removed from the above mixed solution by solvent evaporation at room temperature, after which the solution was washed with 100 ml of distilled water three times, resulting in the elimination of unreacted protamine and obtaining of a white solid sediment. The solid sediment was washed with 100 ml of methanol. After removing unreacted activated DOCA by filtering with a 0.45 μm membrane, a white powder was obtained upon vacuum drying. The remaining unreacted amino acid residue of protamine was eliminated using a one-hour blocking reaction in 100 ml of 1.0 wt % acetaldehyde solution and in 100 ml of 50% methanol solution. After the reaction was finished, unreacted acetaldehyde was removed by washing with distilled water three times and vacuum drying, from which 0.55 g of hydrophobic protamine (protamine-DOCA), in which DOCA was partly coupled with protamine, was obtained.

Example 7

Esterification of Protamine-DOCA

Activated protamine-DOCA (0.5 g) obtained according to the procedure of Example 6 was dissolved in 80 ml Of DMF, and this solution was added immediately to 10 ml of DMF solution containing 1.5 g of DCC. Upon 5 minutes of stirring, DCC was activated and 10 ml of DMF containing 0.84 g of HOSU was added thereto. As the reaction proceeded, a small amount of DCUrea was precipitated. After 24 hours of reaction at room temperature, DCUrea was removed by filtering using a 0.2 μm membrane and DMF was also eliminated from the above solution by solvent evaporation at room temperature. The white powder obtained therefrom was twice washed with 100 ml methanol and filtered with a 0.2 μm membrane, so that a white solid was obtained. The solid was vacuum dried at room temperature for 5 hours. As a result, 0.45 g of hydrophobic protamine (protamine-DOCA) activated by esterification was obtained.

Example 8

Synthesis of Heparin-Protamine-DOCA Conjugate

Activated protamine-DOCA (0.5 g), obtained according to the procedure of Example 7, was dissolved in 100 ml of DMF solution, into which 50 ml of distilled water containing 0.92 g of heparin was loaded. Within 30 minutes after the reaction began, sediment generated by condensation reaction was precipitated, and the generation of the sediment was completed in 30 minutes. When the reaction had continued for 5 hours, distilled water and DMF were removed from the reaction solution by solvent evaporation at room temperature, from which white powder was obtained. The unreacted active protamine-DOCA was removed by dialysis using a cellulose ester membrane and methanol as a solvent. Methanol was substituted with water and filtered using a 0.45 µm membrane, resulting in elimination of unreacted heparin. White sediment obtained therefrom was vacuum dried at room temperature for 12 hours, and finally 1.05 g of white powder was obtained.

Example 9

Activation of Glycocholic Acid

First, 9.3 g of glycocholic acid (referred to as "GOCA" hereinafter) was dissolved in 100 ml of DMF, into which 25 ml of DMF solution containing 6.6 g of DCC was added. Through 5 minutes of stirring, DCC was activated. Next, 25 ml of DMF solution in which 3.7 g of HOSU was dissolved was added thereto. While esterification was going on, DCUrea began to appear and precipitate slowly. After 24 hours of reaction at room temperature, DCUrea was removed by filtering with a 0.2 µm membrane, and the solution was chilled at 5° C. for 12 hours in order for the rest of the DCUrea to be precipitated. The remaining precipitated DCUrea was completely removed in the same manner as explained above. The concentration of the solution was fixed at 15 ml at room temperature, and 100 ml of acetonitrile was added thereto, so as to precipitate a white solid. By filtering the solid with a 0.2 µm membrane, a white powder was obtained, which was then vacuum dried for 5 hours. Finally, 7.0 g of activated GOCA was obtained.

Example 10

Synthesis of Hydrophobic Protamine (Protamine-GOCA)

Protamine (0.5 g) was dissolved in 50 ml of distilled water, into which 50 ml of DMF solution containing 0.31 g of GOCA, obtained according to the procedure of Example 9, was added slowly. After 5 hours of coupling reaction at room temperature, the mixed solution was solvent evaporated to remove distilled water and DMF. The solution was, then, washed with 100 ml of distilled water three times. As a result, unreacted protamine was removed and white solid sediment was obtained. The obtained sediment was washed with 100 ml of methanol and filtered with a 0.45 µm membrane, so as to remove unreacted active GOCA. A white powder was obtained by vacuum drying. The white powder was loaded into 100 ml of 50% methanol solution containing 1.0 wt % acetaldehyde for 1 hour, during which a blocking reaction occurred. The remaining unreacted amino acid residue in protamine was eventually removed therefrom. After the reaction was completed, the solution was washed with distilled water three times, and vacuum dried. Finally, 0.6 g of hydrophobic protamine-GOCA in which GOCA was partly coupled to protamine was obtained.

Example 11

Esterification of Protamine-GOCA

Protamine-GOCA (0.5 g) prepared according to the procedure of Example 10 was dissolved in 80 ml of DMF, and 10 ml of DMF solution containing 1.5 g of DCC was added quickly thereto. During 5 minutes of stirring, DCC was activated, and then 10 ml of DMF solution in which 0.84 g of HOSU was dissolved was added. As the reaction was going on, the small amount of DCUrea was precipitated. After 24 hours of reaction at room temperature, the solution was filtered with a 0.2 µm membrane, which resulted in removing DCUrea, and the filtrate was solvent evaporated at room temperature, which resulted in removing DMF. A white powder obtained therefrom was washed with 100 ml of methanol twice and filtered with a 0.2 µm membrane, from which a white solid sediment was obtained. Through 5 hours of vacuum drying at room temperature, 0.4 g of hydrophobic protamine-GOCA activated by esterification was obtained.

Example 12

Synthesis of Heparin-Protamine-GOCA Conjugate

Activated protamine-GOCA (0.5 g) prepared according to the procedure of Example 11 was dissolved in 100 ml of DMF, and 50 ml of distilled water in which 0.78 g heparin was dissolved was mixed thereto for 5 minutes. Within 30 minutes after the reaction began, sediment was generated by condensation reaction, and the reaction was completed in 30 minutes. After 5 hours of reaction at room temperature, the above solution was solvent evaporated to remove distilled water and DMF. The unreacted active protamine-GOCA was removed from the white powder obtained therefrom by dialysis using a cellulose ester membrane and methanol as a solvent. Methanol was substituted with water and the solution was filtered with a 0.45 µm membrane, thus, the unreacted heparin was removed and white sediment was obtained. The sediment was vacuum dried at room temperature for 12 hours, and finally 0.9 g of white powder was obtained.

Example 13

Synthesis of Polylysine and DOCA Conjugate

First, 1.0 g of polylysine (referred to as "PLL" hereinafter) was dissolved in 50 ml of distilled water, and 50 ml of DMF solution in which 0.98 g of activated DOCA was dissolved was slowly added thereto. After 5 hours of coupling reaction, the solution was solvent evaporated at room temperature, so that distilled water and DMF were removed. The solution was washed with 100 ml of distilled water three times to remove unreacted PLL, resulting in the generation of a white solid sediment. The solid sediment was washed with 100 ml of methanol and filtered with a 0.45 µm membrane to remove unreacted active DOCA. This sediment was further vacuum dried, leading to obtaining a white powder. The white powder was loaded into 100 ml of 50% methanol solution containing 1.0 wt % acetaldehyde for 1 hour, during which a blocking reaction was carried out. As a result, the remaining unreacted amino acid residue of PLL was removed. After the reaction was completed, unreacted acetaldehyde was removed by washing three times with distilled water, and then the solution was vacuum dried, resulting in 1.5 g of hydrophobic PLL-DOCA in which DOCA was partly coupled with PLL.

Example 14

Esterification of PLL-DOCA

PLL-DOCA (1.0 g) prepared according to the procedure of Example 13 was dissolved in 80 ml of DMF, and then, 10 ml of DMF solution containing 2.0 g of DCC was slowly added thereto. Through 5 minutes of stirring, DCC began to be activated, and 10 ml of DMF solution containing 1.12 g HOSU was added again. As the reaction went on, a small amount of DCUrea was generated. After 24 hours of reaction at room temperature, the solution was filtered with a 0.2 μm membrane to remove DCUrea, and the solution was solvent evaporated at room temperature to remove DMF. The white powder obtained therefrom was washed twice with 100 ml of methanol and filtered with a 0.2 μm membrane, so that a white solid sediment was obtained. The sediment was vacuum dried for 5 hours at room temperature. As a result, 0.9 g of PLL-DOCA activated by esterification was obtained.

Example 15

Synthesis of Heparin-PLL-DOCA Conjugate

Activated PLL-DOCA (0.7 g) prepared according to the procedure of Example 14 was dissolved in 100 ml of DMF, and 50 ml of distilled water in which 0.95 g of heparin was dissolved was added thereto for 5 minutes. Within 30 minutes after the reaction began, sediment resulting from the condensation reaction began to be generated, and the reaction was completed in 30 minutes. After 5 hours of reaction at room temperature, the solution was solvent evaporated to remove distilled water and DMF, from which a white powder was obtained. The unreacted active PLL-DOCA was eliminated by dialysis using a cellulose ester membrane and methanol as a solvent. Then, methanol was substituted with water and the solution was filtered with a 0.45 μm membrane to remove unreacted heparin, from which a white sediment was obtained. The sediment was vacuum dried at room temperature for 12 hours, and finally 1.1 g of white powder was obtained.

Example 16

Synthesis of PLL and DOCA Conjugate (PLL-GOCA)

PLL (1.0 g) was dissolved in 50 ml of distilled water, and 50 ml of DMF solution, in which 0.98 g of activated GOCA obtained according to the procedure of Example 9 was dissolved, was added slowly thereto. After 5 hours of coupling reaction at room temperature, the solution was solvent evaporated at room temperature to remove distilled water and DMF. Next, the rest of the solution was washed with 100 ml of distilled water three times, resulting in removal of unreacted PLL, from which a white solid sediment was obtained. This solid sediment was washed with 100 ml of methanol, filtered with a 0.45 μm membrane to remove unreacted active GOCA, and then vacuum dried. As a result, a white powder was obtained. The unreacted amino acid residue remaining in PLL was removed through a one-hour blocking reaction in 100 ml of 50% methanol solution containing 1.0 wt % acetaldehyde. After the reaction was completed, the solution was washed with distilled water three times, so that the unreacted acetaldehyde was removed. By vacuum drying thereof, 1.5 g of hydrophobic PLL-GOCA in which GOCA was partly coupled to PLL was obtained.

Example 17

Esterification of PLL-GOCA

PLL-GOCA (1.5 g) prepared according to the procedure of Example 16 was dissolved in 100 ml of DMF, and then 10 ml of DMF solution in which 1.45 g of DCC was dissolved was added quickly. During 5 minutes of stirring, DCC was activated. Again, 10 ml of DMF solution in which 1.67 g of HOSU was dissolved was added thereto. As the reaction was going on, a small amount of DCUrea was generated. After 24 hours of reaction at room temperature, the solution was filtered with a 0.2 μm membrane to remove DCUrea and was then solvent evaporated at room temperature to remove DMF. The white powder obtained therefrom was washed with 100 ml of methanol twice, and filtered with a 0.2 μm membrane, resulting in obtaining a white solid. The white solid was, then, vacuum dried at room temperature for 5 hours, and finally 1.3 g of PLL-GOCA activated by esterification was obtained.

Example 18

Synthesis of Heparin-PLL-GOCA Conjugate

Activated PLL-GOCA (1.0 g) prepared according to the procedure of Example 17 was dissolved in 100 ml of DMF, and then 50 ml of distilled water containing 0.95 g of heparin was added for 5 minutes. Within 30 minutes after the reaction began, sediment resulting from a condensation reaction began to be generated and the solution became less clear. That reaction was completed in 30 minutes. After 5 hours of reaction, the solution was solvent evaporated at room temperature, resulting in removing distilled water and DMF, from which a white powder was obtained. The unreacted active PLL-GOCA was removed from the white powder by dialysis using a cellulose ester membrane and methanol as a solvent. Then, methanol was substituted with water and the unreacted heparin was removed by filtering the solution with a 0.45 μm membrane. The white sediment obtained therefrom was vacuum dried at room temperature for 12 hours, from which 1.6 g of white powder was obtained.

Example 19

Structure Analysis Using FT-IR Spectrum

To analyze the structures of the hydrophobic multicomponent heparin conjugates synthesized according to the procedures described above, FT-IR spectra (Infrared spectrum, Perkin Elmer Ltd.) were inspected. As a result, in the case of heparin/PAA/ODA conjugate synthesized in Example 3, a C=O double bond, an amide bond, was notable in the range of 170 $cm^{-1}$ of the infrared spectrum, and so was a hydroxyl group of heparin in the range of 3500 $cm^{-1}$, and a methyl group of ODA showed its notable wave length in the range of 2800–2900 $cm^{-1}$.

Example 20

Coating of Hydrophobic Multicomponent Heparin Conjugates

First, 1.0 ml of co-solvent (THF: N,N-dimethyl acetamide, 1:1 v/v %) was added to the 25 mg of hydrophobic multicomponent heparin conjugates synthesized in the Example 3 until the total concentration reached to 2.5 wt %, after which the solution was treated with ultrasonic wave energy at 40° C. for 1 hour, resulting in preparation of a clear solution. The surfaces of an angiocatheter (2.5 cm in diameter, 5 cm in length) made of polyurethane at 25° C. and a glass (0.5 cm.×0.5 cm) were coated once each with the above solution using the dipping coating method. The catheter and the glass coated with hydrophobic multicomponent heparin conjugates were dried at room temperature for 30 minutes, followed by 5 hours of vacuum drying at room temperature, resulting in complete removal of the remaining solvent. Though the coated surfaces of the glass or the catheter were a little unclear, no precipitation phenomenon was observed.

Example 21

Peeling Test of Coated Multicomponent Heparin Conjugates in Aqueous Solution

The glass and the catheter each coated with hydrophobic multicomponent heparin conjugates of Example 3 according to the procedure of Example 20 were put in a Falcon tube filled with 10 ml PBS (pH=7.5, I=0.15) and shaken at 37° C., 100 rpm, for 12 hours. When the reaction was completed, azure A solution (10 mg/ml water) was added thereto, and a dye reaction was carried out (H. J. Conn, "Biological Stains", The Williams and Wilkins., MD, p96–105, 1961). As a result, no color change in the dye solution was detected. Therefore, it is confirmed that if heparin/PAA/ODA, hydrophobic multicomponent heparin conjugates of the present invention are used as coating material, they have great adhesiveness to the materials, like a glass or other high polymers, but have no peeling phenomenon by swelling in aqueous solutions.

Example 22

Azure A Experiment

A glass or a catheter, which had been tested for peeling in Example 21, was immersed in 5 ml azure A solution (10 mg azure A/ml water), after which the solution was suspended at room temperature for 5 hours. As time went by, the surface of a material coated with hydrophobic multicomponent heparin conjugates showed color change, and 5 hours later the dye solution turned a deep purple. Meanwhile, other materials, which were not coated with hydrophobic multicomponent heparin conjugates showed no color change. With those facts, it became certain that hydrophobic multicomponent heparin conjugates stably adhered to the surface of a material while maintaining the unique characteristics of heparin and its associated anti-thrombosis activity.

Example 23

Contact Angle Analysis

A catheter (5 cm) coated with hydrophobic multicomponent heparin conjugates (2.5 wt %) according to the procedure of Example 20 and a catheter without coating were immersed in 10 ml distilled water, and left at room temperature for 5 minutes. As a result, water spreading was observed with the catheter coated with the hydrophobic multicomponent heparin conjugates of the present invention. On the other hand, water spreading of the catheter without coating was decreased, whereas its water contacting angle was increased.

Example 24

Platelet Adherence Experiment

For the platelet adhesion test, platelet-poor-plasma (referred to as "PPP" hereinafter) was separated from a rabbit. More particularly, a New Zealand rabbit (Sunrise Scientific Co.) weighing 2.5 to 3.0 kg, was anaesthetized with ethyl ether, and then, 36 ml of blood was drawn with a 50 ml syringe using the cardiac puncture method. Four ml of 3.8% sodium citrate had been put in that syringe in advance to prohibit blood clotting. The blood was centrifuged at 4° C. at 1440 rpm for 10 minutes, from which a fresh rabbit PPP was obtained. The platelet concentration in plasma was measured with a Coulter counter (Coulter electronics Ltd, UK), and the preferred concentration of platelets was $4.2 \times 10^5$ cells/µl. The separated PPP was used for the test within 3 hours after preparation. A glass (0.5×0.5 cm) coated with hydrophobic multicomponent heparin conjugates of the present invention (2.5 wt %) and a control glass without coating were put into tubes each having 1 ml of separated fresh rabbit PPP, which were suspended in a 37° C. stirring water bath for 1 hour. One hour later, PPP was removed from each tube and the glasses were washed with PBS three times for complete removal of PPP. Each of the above glasses was treated with 3 ml of 2.5% glutaraldehyde for platelet fixing for 4 hours, after which they were washed with aqueous ethanol (EtOH) solution according to the following steps: Step 1, 5 ml 50% EtOH for 1 hr; step 2, 5 ml 80% EtOH for 1 hr; and step 3, 5 ml 100% EtOH for 1 hr. Each glass from which ethyl alcohol was removed was treated with liquid nitrogen, and thereafter freeze-dried for 6 hours. Each glass was observed with scanning electron microscopy (SEM) to check platelet adhesion. As a result, it was confirmed that blood compatibility of the glass coated with hydrophobic multicomponent heparin conjugates of the present invention was largely improved, compared to the control glass.

Example 25

Blood Clotting Experiment

For the blood-clotting test, whole blood was separated from a rat. Particularly, a Sprague-Dawley rat weighing 250–300 g (Korea Biolink) was anaesthetized with ethyl ether, and then, 3.6 ml blood was taken with a 50 ml syringe, into which 0.4 mg of 3.8% sodium citrate had been placed to prevent clotting, using the cardiac puncture method. The blood was used for the test immediately after being taken.

A blood vessel catheter (1 cm long) coated with 25 mg of hydrophobic multicomponent heparin conjugates (2.5 wt %) synthesized according to the procedure of Example 9 and another similar catheter without coating were immersed in whole blood of a rat prepared as mentioned above for 1 hour and then, washed gently with distilled water and photographed immediately thereafter. The result was that the catheter coated with hydrophobic multicomponent heparin conjugates of the present invention showed no aggregation of blood components at all, while the control catheter without coating had strong aggregation of blood components in 1 hour after immersion.

INDUSTRIAL APPLICABILITY

As shown above, the hydrophobic multicomponent heparin conjugates of the present invention are only soluble in specific organic solvents, and they can be easily coated to macromolecules or the surface of metal by the methods of solvent evaporation, dip coating, or spraying. These conjugates are not soluble in water, thus they can be stably used in clinical treatment after coating. Furthermore, the hydrophobic multicomponent heparin conjugates of the present invention keep their original characteristics of anti-thrombus activity after being coated on the substrate. More precisely, the conjugates enhance the anti-thrombus activity of the coated surfaces by inhibiting blood clotting on the coated surfaces. Further, the hydrophobic multicomponent heparin conjugates of the present invention permit the coated substrates to become wet by decreasing the frictional coefficient of the coated surfaces, thus increasing the water-absorption capacity of the coated surfaces. Thus, the hydrophobic multicomponent heparin conjugates of the present invention can be very useful as coating agents for inhibiting the side-effects of thrombi and modifying the surfaces of artificial organs and medical devices contacting blood, for example, catheters, insertion tubes, etc.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A hydrophobic heparin conjugate wherein heparin is covalently bonded to multiple macromolecules containing multiple functional groups therein, and wherein multiple hydrophobic materials selected from the group consisting of octadecylamine (ODA), alkanoic amines, bile acids, sterols, and alkanoic acids are covalently bonded to each macromolecule through the functional groups.

2. The hydrophobic heparin conjugate of claim 1, wherein the macromolecules are selected from the group consisting of synthetic macromolecules, proteins, biopolymers, and mixtures thereof.

3. The hydrophobic heparin conjugate of claim 2, wherein the synthetic macromolecules are selected from the group consisting of polydienes, polyalkenes, polyacetylenes, polyacrylic acid, poly(α-substituted acrylic acid), polyvinyl ethers, polyvinyl alcohol, polyvinyl halides, polystyrene, polyoxides, polyethers, polyesters, polycarbonates, polyamides, polyureas, polyurethanes, polyimines, polysulfides, polyphosphates, polysiloxanes, polysilsesquioxanes, polyheterocyclics, and copolymers thereof.

4. The hydrophobic heparin conjugate of claim 2, wherein the proteins are selected from the group consisting of protamine, poly(amino acids), and copolymers thereof.

5. The hydrophobic heparin conjugate of claim 2, wherein the biopolymers are selected from the group consisting of polysaccharides, gelatin, collagen, alginate, hyaluronic acid, alginic acid, carrageenan, chondroitin, pectin, chitosan, cellulose, and copolymers thereof.

6. The hydrophobic heparin conjugate of claim 1, wherein the hydrophobic materials have more than one reactive functional group and under 100 mg/ml water solubility after being covalently bonded to the macromolecules.

7. The hydrophobic heparin conjugate of claim 1, wherein the heparin is recombinant heparin.

8. A method for preparing the hydrophobic heparin conjugate of claim 1, comprising: 1) covalently binding macromolecules comprising multiple functional groups therein to heparin; and 2) covalently binding multiple hydrophobic materials selected from the group consisting of octadecylamine (ODA), alkanoic amines, bile acids, sterols, and alkanoic acids to the functional groups of the macromolecules covalently bonded to heparin; and 3) isolating the hydrophobic heparin conjugates.

9. The method of claim 8, wherein the covalent binding of macromolecules to heparin comprises forming a covalent bond using functional groups selected from the group consisting of hydroxyl, carboxyl, amine, thiol, and azide.

10. The method of claim 8, wherein covalent binding of the hydrophobic materials to the functional groups comprises forming a covalent bond using functional groups selected from the group consisting of hydroxyl, carboxyl, amine, thiol, and azide.

11. The method of claim 8, wherein the covalent binding comprises forming bonds selected from the group consisting of non-degradable bonds and degradable bonds, wherein the non-degradable bonds are members of the group selected from amide bonds and urethane, and the degradable bonds are members selected from the group consisting of ester bonds and anhydride bonds.

12. A coating agent for modifying the surfaces of artificial organs and medical instruments, comprising the hydrophobic heparin conjugate of the claim 1.

* * * * *